US00PP25937P2

(12) United States Plant Patent
Saul

(10) Patent No.: US PP25,937 P2
(45) Date of Patent: Sep. 22, 2015

(54) ***CORTADERIA* PLANT NAMED 'BLUE BAYOU'**

(50) Latin Name: *Cortaderia selloana*
Varietal Denomination: Blue Bayou

(71) Applicant: Robert Mark Saul, Atlanta, GA (US)

(72) Inventor: Robert Mark Saul, Atlanta, GA (US)

(73) Assignee: ITSAUL PLANTS, LLC, Alpharetta, GA (US)

( * ) Notice: Subject to any disclaimer, the term of this patent is extended or adjusted under 35 U.S.C. 154(b) by 169 days.

(21) Appl. No.: 13/998,384

(22) Filed: Oct. 28, 2013

(51) Int. Cl.
*A01H 5/02* (2006.01)

(52) U.S. Cl.
USPC ..... Plt./384

(58) Field of Classification Search
USPC ..... Plt./384
See application file for complete search history.

*Primary Examiner* — Anne Grunberg
(74) *Attorney, Agent, or Firm* — Penny J. Aguirre

(57) ABSTRACT

A new cultivar of *Cortaderia selloana* named 'Blue Bayou', that is characterized by its narrow foliage that is tinted blue in color, its average foliar height of 1.2 m, average foliar width of 1.5 m, and average bloom height of 2 m, its multiple blooms in the first spring of growth from culm divisions made in the fall or winter or from tissue cultured plants planted in fall, and its clean foliage with no disease or leaf spot observed and its flowers that are white to creamy white in color.

2 Drawing Sheets

Botanical classification: *Cortaderia selloana.*
Varietal denomination: 'Blue Bayou'.

BACKGROUND OF THE INVENTION

The present invention relates to a new and distinct cultivar of *Cortaderia selloana* and will be referred to hereafter by its cultivar name, 'Blue Bayou'. 'Blue Bayou' represents a new cultivar of pampas grass, a perennial ornamental grass grown for landscape use.

The Inventor discovered the new cultivar, 'Blue Bayou' in the summer of 2010 as a culm sport of *Cortaderia selloana* 'Pumila' (not patented) that was growing in a garden in Alpharetta, Ga.

Asexual propagation of the new cultivar was first accomplished by culm division in June 2010 in Alpharetta, Ga. by the Inventor. Asexual propagation by culm division and tissue culture has shown that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'Blue Bayou' as a new and unique cultivar of *Cortaderia.*

1. 'Blue Bayou' exhibits narrow foliage that is tinted blue.
2. 'Blue Bayou' exhibits an average foliar height of 1.2 m, an average foliar width of 1.5 m, and an average bloom height of 2 m.
3. 'Blue Bayou' exhibits multiple blooms in the first spring of growth from culm divisions made in the fall or winter.
4. Tissue culture liners of 'Blue Bayou' planted from fall to the start of winter will finish a three-gallon pot by spring and bloom the first summer.
5. 'Blue Bayou' exhibits clean foliage with no disease or leaf spot observed.

6. 'Blue Bayou' exhibits flowers that are white to creamy white in color.

The parent plant of 'Blue Bayou', 'Pumila', is similar to 'Blue Bayou' in plant height and stature. 'Pumila' differs from 'Blue Bayou' in having wider foliage that is less blue in color. Side-by-side growth comparisons of tissue culture liners of 'Blue Bayou' and 'Pumila' were made. Liners were potted in three-quart pots in a greenhouse in April (late season) and shifted outside to three-gallon pots in June. Plants of 'Blue Bayou' matured more quickly than those of 'Pumila' and had 2 to 3 times the number of culms per pot at summers end. About 20% of the late season 'Blue Bayou' plants bloomed with large attractive blooms. Almost all plants of 'Pumila' bloomed, however the blooms were unattractive and about half the normal size. 'Blue Bayou' can be most closely compared to typical plants of the species *Cortaderia selloana* and 'Scarlet Wonder' (U.S. Plant Pat. No. 19,015). Typical plants of the species are similar to 'Blue Bayou' in having a similar overall plant habit, however they differ from 'Blue Bayou' in being taller in height and in having wider, longer foliage that is medium green in color. 'Scarlet Wonder' differs from 'Blue Bayou' in having flowers that are purple in color.

BRIEF DESCRIPTION OF THE DRAWINGS

The accompanying colored photographs illustrate the overall appearance and distinct characteristics of the new *Cortaderia*. The photographs were taken of three year-old plants of the new cultivar as grown in a garden in Atlanta, Ga.

The photograph in FIG. 1 illustrates the overall habit and appearance of 'Blue Bayou'.

Figure 1:
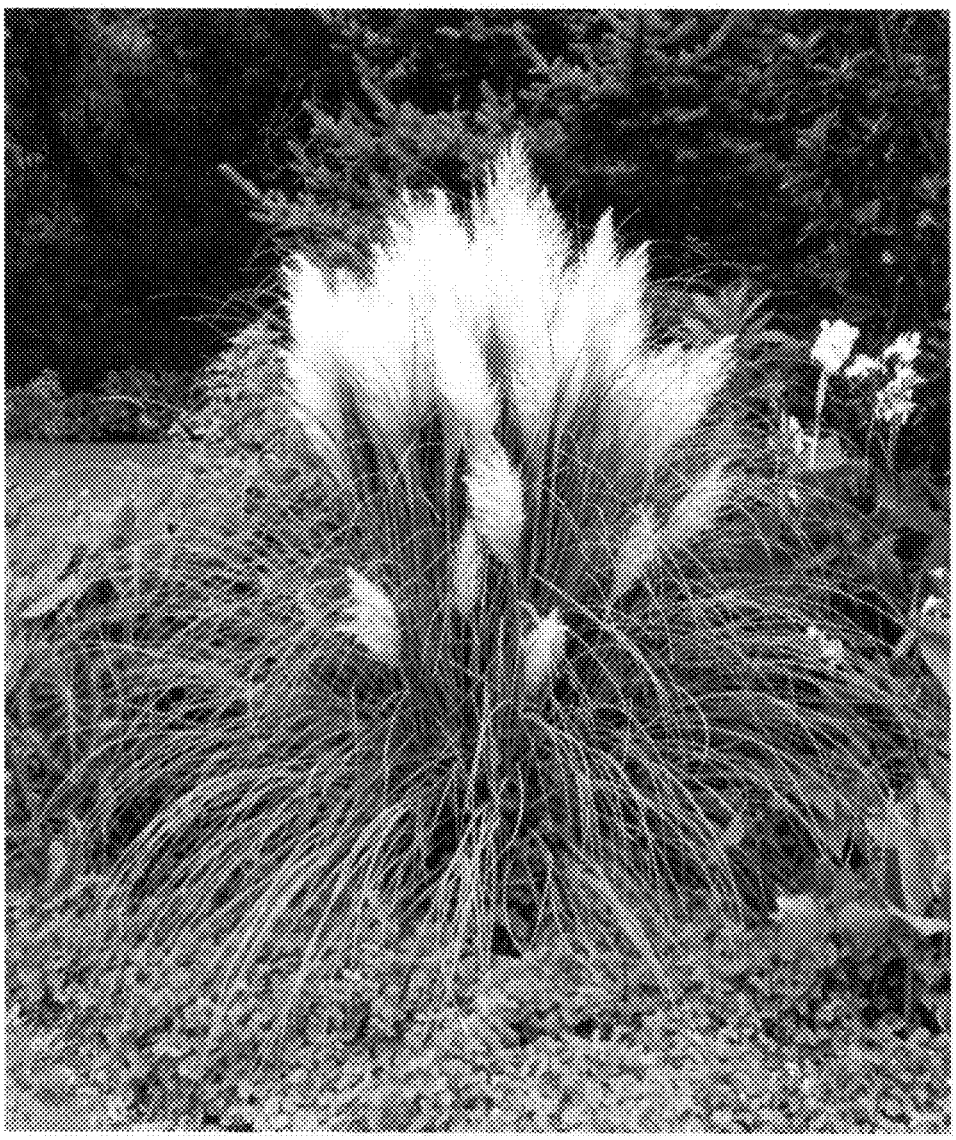
Figure 2:
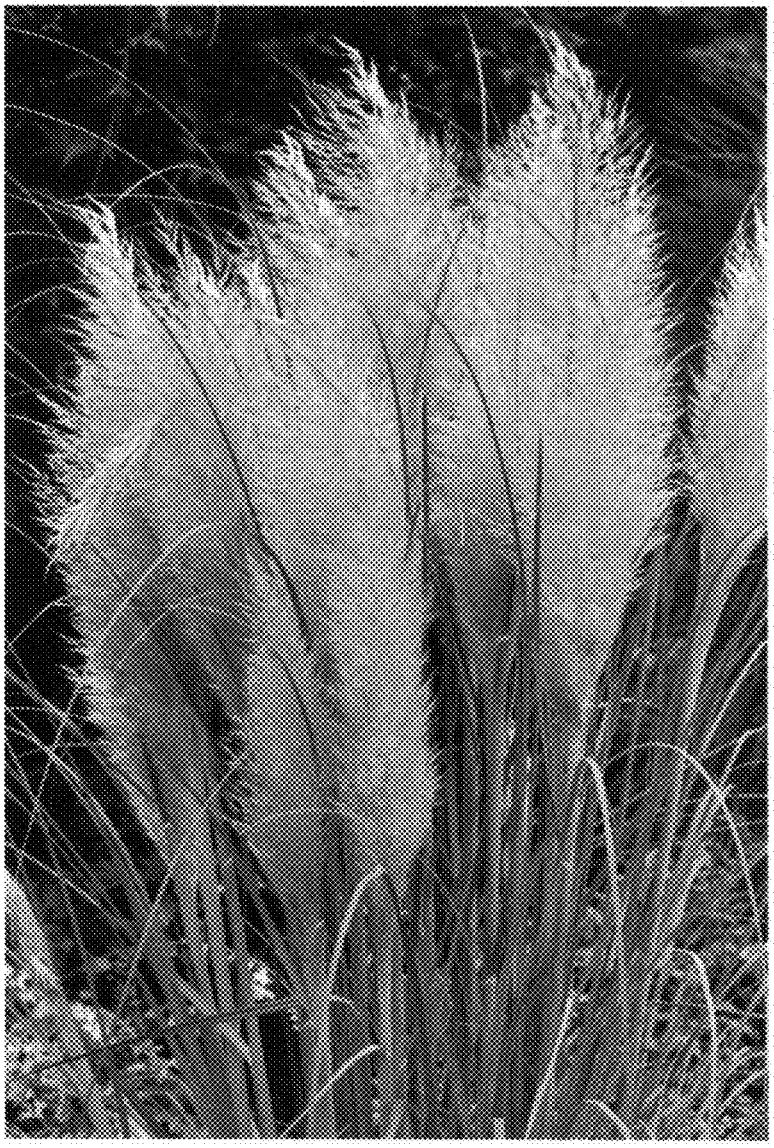

The photograph on FIG. 2 provides a view of the inflorescences of 'Blue Bayou'.

The colors in the photographs are as close as possible with the photographic and printing technology utilized. The color values cited in the detailed botanical description accurately describe the colors of the new *Cortaderia.*

DETAILED BOTANICAL DESCRIPTION

The general observations and descriptions describe plants that were about two years in age as grown outdoors in a 3-gallon container in Alpharetta, Ga. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—From May to mid-June with a second blooming period in late August in Georgia, multiple blooms are produced in the first spring of growth from culm divisions made in the fall or winter or from tissue cultured plants planted in fall.

*Plant habit.*—Herbaceous, tussock-forming, ornamental grass with stout culms and leaf blades that cascade in a vase-shaped form with upright showy inflorescences.

*Height and spread.*—Average foliar height of 1.2 m, an average foliar width of 1.5 m, and an average bloom height of 2 m in three years of growth from a culm division in a garden.

*Cold hardiness.*—U.S.D.A. Zones 6 to 10.

*Diseases.*—Plants have been observed to be disease free with no leaf spot observed.

*Root description.*—Fibrous, deep rooted.

*Propagation.*—Culm division or tissue culture (preferred).

*Growth rate.*—Vigorous.

Culm (stem) description:

*General.*—Rounded, enclosed by leafs sheathed to base.

*Culm aspect.*—Held upright to about a 45° angle.

*Culm color.*—161B in color on upper portion (not sheathed) with markings of 174, sheathed portion is 138B with fine striations of 138A (defined by leaves).

*Culm size.*—Up to 1 cm in width (at base) and 90 cm in height (including rachis).

*Culm surface.*—Glabrous.

*Culm number.*—About 2 flowering culm surrounded by about 14 tufts of foliage as grown in a one-gallon container.

*Internode length.*—Average of 7 cm between leaf blades.

*Ligule.*—Comprised of short silky hairs, 1 mm in width, 158B in color.

Foliage description:

*Leaf shape.*—Linear.

*Leaf division.*—Simple.

*Leaf base.*—Sheathed to base.

*Leaf arrangement.*—Tufted (2-ranked).

*Leaf apex.*—Acuminate.

*Leaf aspect.*—Emerging leaves are erect, leaf blades diverge from leaf sheath at ligule at about a 40° angle from center of flowering culm and then cascade, on non-flowering tufts the leaves are upright to 45° from ligule.

*Leaf venation.*—Parallel, color matching leaf coloration on upper and lower surface on leaf blades, 138A in color on shafts.

*Leaf margins.*—Entire, visibly smooth but serrated with very sharp short teeth are present that point in a forward direction.

*Leaf persistence.*—Evergreen in mild climates, dries but is persistent in colder regions.

*Leaf attachment.*—Sheathed, leaf is sheathed from the base of culm and the blade extends out from the culm at a ligule.

*Leaf blade size.*—On flowering culms; shaft an average of 50 cm in length with blade an average of 40 cm in length and 1.5 cm in width and tapering to a point at the apex, on tufted leaves; shaft about 16 cm in length to ligule with the blade up to 60 cm in length and an average of 6 mm in width.

*Leaf surface.*—Glabrous and dull on upper and lower surface.

*Leaf number.*—Flowering culm; Average of 5 per culm, on non flowering tufts; an average of 9.

*Leaf blade color.*—Young leaves, upper and lower surface; 144A, mature leaves, upper surface and lower surface; N138A.

*Leaf shaft color.*—145B with veins 138A and tinted at base with 187A.

Flower description:

*General description.*—Feathery panicle terminating from culm comprised of numerous pistillate spikelets enclosed by hair-like lemmas.

*Fragrance.*—None.

*Panicle size.*—Average of 37 cm in length and 9.5 cm in width.

*Panicle color.*—A blend of 161B and 158D.

*Rachis description.*—Strong, 158A in color, average of 30 cm in length and 2.2 cm in width, held upright, internodes jointed.

*Spikelet description.*—Pedicillate, palea surrounded by 1 lemma bearing a long awn, glumes longer than lower florets.

*Spikelet number.*—About 20,000 per panicle.

*Spikelet size.*—About 2 cm in length and 1.3 cm in width.

*Glume.*—2 per spikelet, about 1 cm in length and 0.8 mm in width, 155D in color, lanceolate in shape.

*Lemma.*—1 per spikelet, an average of 1.2 cm in length and 0.5 mm in width, 155D in color, covered in wispy hairs, an average of 6 mm in length and too narrow in width to measure, 155D in color.

*Palea.*—1 per spikelet, an average of 4 mm in length and 0.3 mm in width, 155D in color.

Reproductive organs:

*Androecium.*—Not present, pistillate florets only.

*Gynoecium.*—1 Pistil, 2 stigmas, are feathery and 165B in color when mature, ovary is superior, minute and 165C in color.

*Caryopsis.*—No caryopsis production was observed.

It is claimed:

1. A new and distinct cultivar of *Cortaderia* plant named 'Blue Bayou' as herein illustrated and described.

* * * * *